(12) United States Patent
Rosenman et al.

(10) Patent No.: US 7,840,261 B2
(45) Date of Patent: Nov. 23, 2010

(54) CATHETER SYSTEMS AND METHODS FOR PLACING BI-VENTRICULAR PACING LEADS

(75) Inventors: Daniel C. Rosenman, South San Francisco, CA (US); R. Hardwin Mead, South San Francisco, CA (US); Peter A. Altman, South San Francisco, CA (US)

(73) Assignee: BioCardia, Inc., San Carlos, CA (US)

( * ) Notice: Subject to any disclaimer, the term of this patent is extended or adjusted under 35 U.S.C. 154(b) by 813 days.

(21) Appl. No.: 10/163,951

(22) Filed: Jun. 5, 2002

(65) Prior Publication Data

US 2003/0229386 A1 Dec. 11, 2003

(51) Int. Cl.
*A61N 1/372* (2006.01)

(52) U.S. Cl. .......................................... 607/2

(58) Field of Classification Search ................ 607/119, 607/122; 600/374, 585; 606/129, 108; 604/528; 128/899
See application file for complete search history.

(56) References Cited

U.S. PATENT DOCUMENTS

| | | | |
|---|---|---|---|
| 4,798,598 A | 1/1989 | Bonello et al. ............. 604/280 |
| 4,997,424 A * | 3/1991 | Little .......................... 604/161 |
| 5,203,772 A * | 4/1993 | Hammerslag et al. ....... 604/528 |
| 5,639,276 A * | 6/1997 | Weinstock et al. .......... 606/129 |
| 5,882,333 A * | 3/1999 | Schaer et al. ............ 604/95.01 |
| 5,993,462 A * | 11/1999 | Pomeranz et al. ........... 606/129 |
| 6,159,198 A | 12/2000 | Cardeski et al. ............. 604/523 |
| 6,165,163 A | 12/2000 | Chien et al. ................. 604/523 |
| 6,210,408 B1 * | 4/2001 | Chandrasekaran et al. .... 606/41 |
| 6,219,582 B1 | 4/2001 | Hofstad et al. .............. 607/122 |
| 6,224,587 B1 * | 5/2001 | Gibson ....................... 604/528 |
| 6,251,119 B1 | 6/2001 | Addis ........................ 606/167 |
| 6,277,107 B1 | 8/2001 | Lurie et al. ................. 604/528 |
| 6,280,433 B1 * | 8/2001 | McIvor et al. .............. 604/524 |
| 6,522,933 B2 * | 2/2003 | Nguyen ..................... 607/116 |
| 6,589,164 B1 * | 7/2003 | Flaherty .................... 600/121 |
| 6,659,981 B2 * | 12/2003 | Stewart et al. ........ 604/164.02 |

* cited by examiner

*Primary Examiner*—Scott M Getzow
*Assistant Examiner*—Amanda Patton
(74) *Attorney, Agent, or Firm*—K. David Crockett, Esq.; Crockett & Crockett, PC

(57) ABSTRACT

A catheter system suitable for implanting pacemaker leads. A guide catheter is provided with steering capability, and the necessary steering components are modified to permit the catheter to be sliced during withdrawal, so that the proximal forced applied to the pacemaker lead is minimized and the lead is less likely to be dislodged.

9 Claims, 4 Drawing Sheets

CATHETER SYSTEMS AND METHODS FOR PLACING BI-VENTRICULAR PACING LEADS

FIELD OF THE INVENTIONS

The devices and methods described below relate to the catheters and methods of using catheters.

BACKGROUND OF THE INVENTIONS

Implanted cardiac pacemakers are used to detect abnormal heart rhythms and apply electrical shocks to the heart to keep the heart beating at a desired pace. They have typically been implanted with the leads attached to the right side of the heart (due to ease of placement), but bi-ventricular pacing has recently been developed to provide better pacing efficiency, heart output and patient quality of life. In bi-ventricular pacing, one lead is placed in electrical contact with the right ventricle, and a second lead is placed in electrical contact with the left ventricle. These leads are embedded into the heart, and their placement may be achieved surgically (for epicardial placement) and percutaneously (mostly through the right side of the heart and the venous system). Bi-ventricular pacing leads include one that is placed through the venous system through the coronary sinus into a vein that is outside of the left ventricle (still epicardial, but placed in a vein).

Access the coronary sinus is quite difficult. The prior art method of placing the second pacemaker lead into the left side of the heart entails placing a guide wire or electrophysiology catheter percutaneously into the coronary sinus, then placing a guide catheter over the guide wire or EP catheter into the coronary sinus. Once the distal tip of the guide is seated in the coronary sinus, the EP catheter is removed. Then, a balloon occlusion/infusion catheter is inserted into the guide and into the coronary sinus. The balloon infusion catheter is used with a guide wire to sub-select venous branches. Venograms are done to image the venous system of the heart under fluoroscopy. The balloon on the infusion catheter is inflated during the venograms to prevent the contrast fluid (which can be infused through either the guide or the infusion catheter) from being carried out of the venous system too quickly by the normal venous flow (the contrast agent used for the venogram is injected against the flow of blood in the coronary sinus). After the venogram, the balloon is deflated. When the desired location for the lead is identified (it may be one of several coronary veins, of a site within the coronary sinus itself), the balloon infusion catheter is removed and discarded, leaving the guide catheter in place within the coronary sinus.

To place the lead, which includes an implantable tip and 20 to 25 inches of lead wire, the lead in inserted into the guide catheter and advanced to the implantation site. The leads may be tracked over a guide wire (over the wire or monorail systems are used), or pushed over a stylet. The guide wire or styletted lead is inserted through the guide and manipulated to the vein chosen for placement. Additionally, injection of contrast agent may help to visualize the venous system during placement, but the balloon catheter is no longer present to prevent the contrast agent from being quickly flushed from the site of interest.

Once the lead is in place and has been electrically tested, the doctor does not want to disturb it. The guide sheath must be removed from the body, which entails dragging it over the pacemaker lead, and this imparts force on the pacemaker lead which may dislodge the tip from its implantation site. Thus the guide catheter may be provided in a slittable or tear-away form, so that the length of pacemaker lead subject to the dragging forces of the guide catheter is minimized. The doctor maintains control of the proximal end of the lead and pulls or peels the sheath/guide while he is withdrawing it from the body over the lead. When finished, the lead gets connected to a defibrillator/pacemaker that is implanted in a pocket under the patient's skin.

SUMMARY

The devices and methods described below provide for pacemaker lead placement while minimizing the number of catheter exchanges required. A guide catheter is provided with a steerable tip which is operated with a lever on a handle which is fixed to the proximal end of the catheter. The handle is fixed in a manner which leaves sufficient extent of the catheter tube exposed so that it may be cut while in place. The catheter may include a deflection tube disposed within the distal tip, which controls the bending behavior of the distal tip, and this deflection tube may be modified to make it easy to cut. The guide catheter can be used to install pacemaker leads or other devices, and then may be removed from the body by pulling it proximally while cutting it open. This minimizes the proximal force imparted to the pacemaker lead so that the lead will not be dislodged by removal of the guide catheter.

DETAILED DESCRIPTION OF THE INVENTIONS

Figure 1:
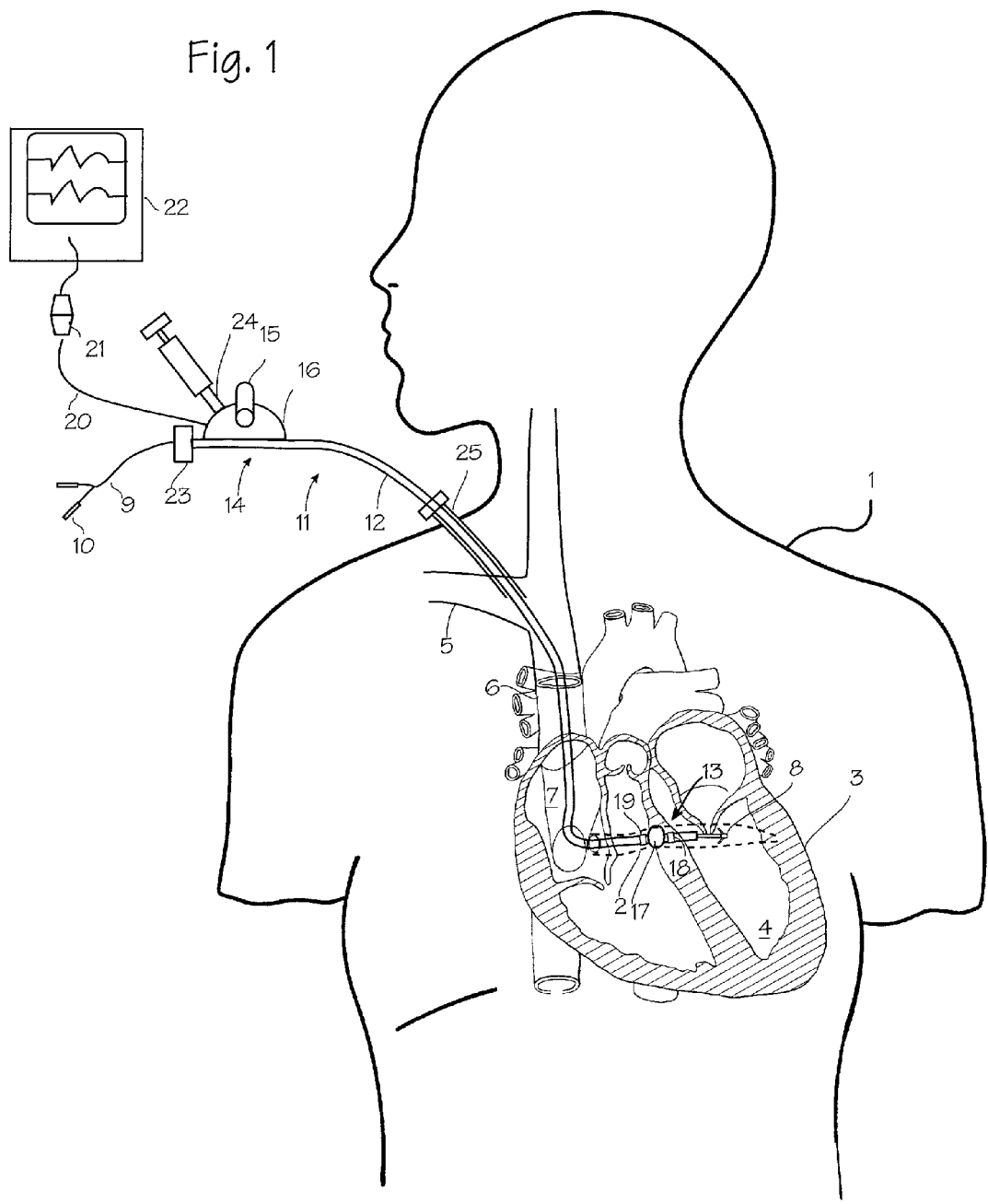
FIG. 1 illustrates an exemplary use of the catheter and method especially adapted for placement of devices in the human body.

FIG. 1 illustrates an exemplary use of the catheter and method especially adapted for placement of devices in the human body. The patient 1 is undergoing a catheterization of the coronary sinus 2, which is the primary venous drainage vessel of the heart 3 in order to place a pacemaker lead into the left ventricle 4. Access to the coronary sinus is gained percutaneously, through the subclavian vein 5, the superior vena cava 6, and the right atrium 7. The goal of the catheterization is to place a pacemaker lead tip 8 into the left ventricle (or a location from which it can pace or stimulate the left ventricle), while temporarily leaving the pacemaker lead wire 9 itself in the tortuous venous pathway and leaving the pacemaker connectors 10 just outside the body. To achieve this, guide catheter 11 has been placed in the patient through the vasculature so that its distal tip is disposed within the coronary sinus. In the typical pacemaker lead placement, the connectors and the lead wire will eventually be completely inserted into the body, and connected to an implanted pacemaker.

The guide catheter 11 includes a guide catheter tube 12 with a distal section 13 and a proximal section 14. The distal section of the catheter is adapted for insertion into the vasculature, and has a steerable tip which is controlled from the catheter proximal end with the pullwire operator 15 on the handle 16. The handle is securely fastened to the catheter, around a proximal segment of the catheter tube, but only partially surrounds the catheter body, leaving a small circumferential region of the catheter exposed outside the handle. The catheter has a balloon 17 disposed on the distal tip, along with one electrode 18 mounted immediately distal to the balloon and a second electrode 19 mounted on the catheter immediately proximal to the balloon (additional electrodes may be used). The electrodes are connected through conductor 20 and connector 21 to EKG display 22, and may be used in conjunction with the EKG display by the surgeon performing the procedure to help determine when the distal end of the guide catheter has entered the vena cava, ventricle or coronary sinus. The electrodes are adapted for sensing EKG signals emanating from body tissue. The EKG signal picked up by the electrodes, when in contact with the walls of blood vessels, the heart wall, and vena cava are readily distinguishable. The catheter also includes a hemostatic fitting 23 through which the pacemaker lead and tip can be passed and a balloon inflation fitting 24 which connects to a balloon inflation lumen which is in fluid communication with the balloon. The pacemaker lead has been inserted through a guide catheter. The guide catheter itself has been inserted into the subclavian vein using the guide sheath 25 using a standard insertion technique such as the Seldinger technique. As described below, the catheter is adapted for easy withdrawal from the body while minimizing the force exerted on the pacemaker lead wire, thereby minimizing the risk of disturbing the pacemaker lead.

Figure 2:
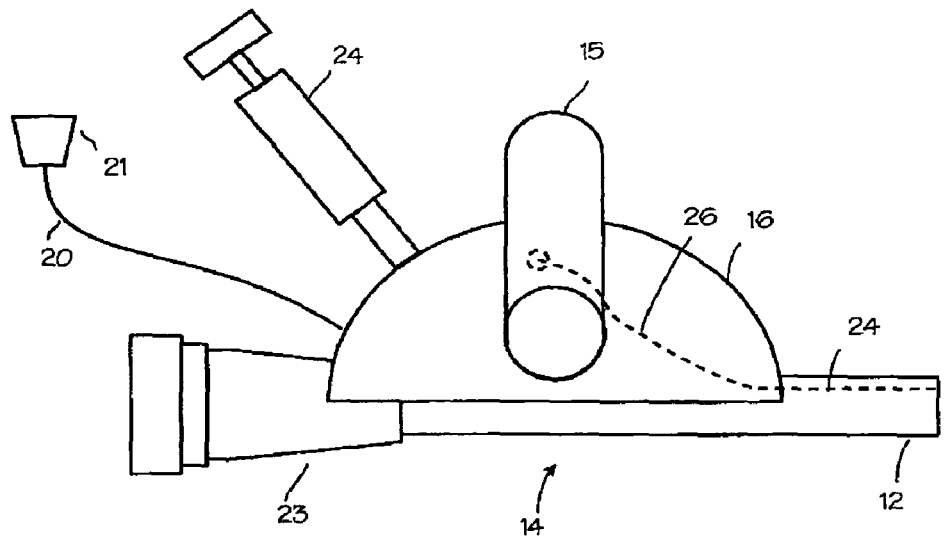
FIG. 2 is a view of the proximal portion of the catheter.

FIG. 2 more clearly illustrates the proximal section of the catheter 11, including the catheter body tube 12, the EP connector 21, pullwire operator 15, handle 16, hemostatic fitting 23, and the balloon inflation fitting 24. The handle may be provided in any shape, and preferably is provided in an ergonomic form which permits easy grasping and manipulation as described below. The handle is attached to the catheter body tube in a manner that leaves a circumferential portion of the catheter body exposed. The pullwire operator is illustrated as a lever fixed to pull the pullwire so that operation of the lever results in deflection of the distal tip of the catheter, and any other form of pullwire operator may be used. The steering pullwire 26 is disposed within the guide catheter tube, and exits the tube near the pullwire lever, and is attached at its distal end to the pullwire lever operator.

Figure 3:
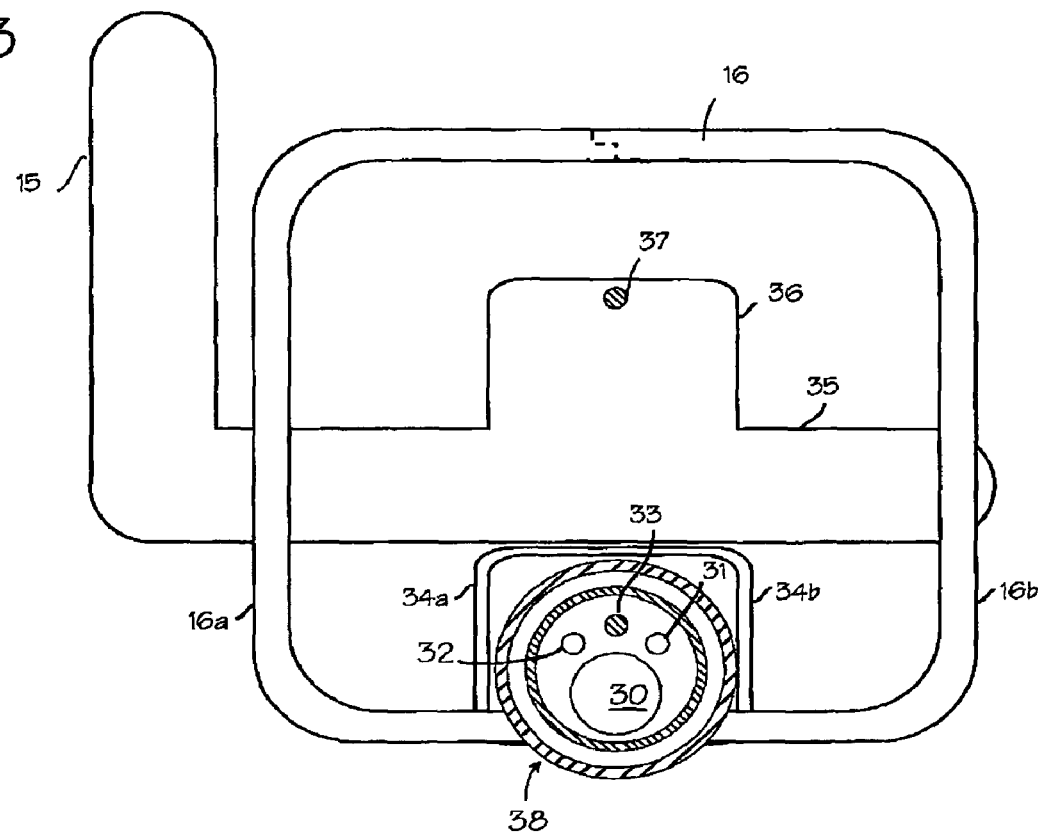
FIG. 3 shows a transverse cross section of the proximal portion of the catheter.

FIG. 3 shows a cross section of the proximal section. The catheter body tube includes a lumen 31 for passage of the pacemaker lead, a lumen 30 for balloon inflation, a lumen 32 for the EP electrode conductors, and a lumen 33 for the steering pullwire 26 used to operate the steerable tip of the guide catheter. The handle 16 comprises two sections, 16a and 16b, and each section includes a clamp member 34a and 34b which close upon the catheter tube when the handle is assembled. The pullwire operator 15 is mounted on a pin 35, which can be provided with a cam 36, and the steering pullwire is secured to the pin or cam at an anchor point 37. The position of the anchor point is dictated by the desired responsiveness of the steerable tip to lever movement. The pacemaker lead lumen 30 is disposed off center within the catheter tube, and the thin walled side of the catheter tube is disposed outside the clamping members. The thin walled region on the catheter body is radially displaced from the pullwire and pullwire lumen (in this case, it is directly opposite the pullwire), and aligned with the exposed portion of the catheter tube. In this illustration, it can be seen that the catheter tube is partially disposed within a channel within the handle, and that the circumferential portion 38 of the catheter tube is exposed through the channel opening between the two halves of the handle. The channel may have a narrow opening, with a width less that the width of the channel, as shown (so that the channel traps the catheter tube), or, if the catheter tube is otherwise fixed within the channel, the opening of the channel may be about the same diameter, or even larger than, the catheter body. The catheter tube may be fixed within the channel with glue, it may be melted or heat sealed to the handle, or it may be held in place with releasable or readily cut straps or clamps arms, or a thin over-molded extension of the handle material which covers the channel with a thin, easily cut layer of material, or is itself peelable from the remainder of the handle.

Figure 4:
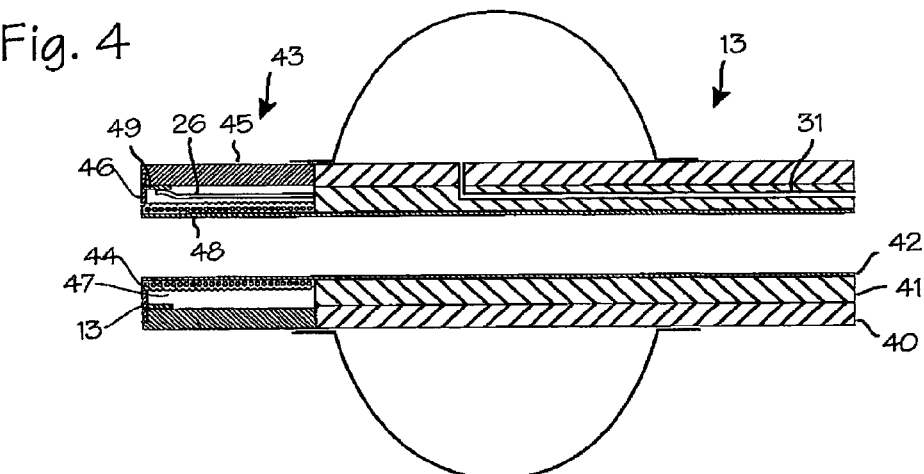
FIG. 4 shows a longitudinal cross-section of the distal section of the guide catheter.

FIG. 4 is a longitudinal cross section of the distal segment of the guide catheter tube. The external details of the distal segment are similar to those shown in FIG. 1, including the balloon 17, distal sensing electrode 18 and proximal electrode 19. The balloon inflation lumen 31 inside the catheter provides for fluid communication between the balloon and the balloon inflation connector. The steering pullwire 26 is disposed within the catheter body. Preferably, the guide catheter tube 12 is comprised of an outer shaft and an inner tube, as shown in FIG. 4. The outer catheter shaft 40 is typically Pebax that is between 72 D and 25 D in durometer or hardness. It is reinforced with braiding that is composed of small diameter plastic braided in an overlapping pattern for strength, flexibility and torque transmission. Plastic is chosen for the braid because it may be cut easily in the method described herein, but other suitable materials such as stainless steel and nitinol may be used. The outer catheter shaft 40 is typically 0.118", in outer diameter, 0.091" in inner diameter and 40 to 150 centimeters in length. The inner tube 41 is a multi-lumen Pebax tube which may also be braided for reinforcement (that is, one or both of the outer shaft and inner tube may be reinforced).

The liner 42 is typically polytetrafluoroethylene with an inner diameter of 0.072". Its outer diameter is sized to slip fit within the inner diameter of the outer catheter shaft 40. A groove for receiving the pullwire may be cut in the outer wall of the inner tube or in the inner wall of the outer catheter shaft. The two shafts and liner may then be melted, bonded, pulltruded, glued or welded to make a unitary tube with a central lumen and eccentric lumens for the pullwire, EP electrode conductors and balloon inflation fluid.

At the distal end of the device, the guide catheter inner tube 41 is joined to a distal assembly 43. The distal assembly comprises a covered coil 44, an outer tube extension 45, and soft tip 46. The covered coil may comprise a stainless steel round wire compression spring, typically 0.080" outside diameter by 0.075" inside diameter and 1.5" in length with a coil spacing of 0.015" and a round wire diameter of about 0.0025" (so that it may be readily cut by the cutter). The coil 44 is covered on the outside by a length of 35 D Pebax tubing 47 that has been heat fused through the windings of the coil 44 until it adheres to the distal section of the fluoropolymer liner 48 that is inside the coil 44. The fluoropolymer liner 42 is typically polytetrafluoroethylene that is between 0.0005" and 0.002" thick, etched on the outside by chemical etchant and slip fit to the inside of the compression spring coil 44 (it may also comprise an extension of inner tube 41). The heat fusing of the Pebax tube 47 through the coil 44 to the fluoropolymer liner 48 makes this distal assembly a unitary composite. The pullwire 26 is connected to the distal end of the catheter, and may be fixed to an anchor 49 (which may be a ring, partial cylinder or half-pipe), or any other suitable means of fixation. The bending direction may be controlled with the inclusion stiffener on one side of the catheter, and the stiffener may be provided in the from of a length of metal or plastic (flat or arcuate) disposed radially opposite the pullwire.

The distal end of the catheter may be preformed with a bend, located about 5 cm from the distal tip of the catheter, of about 45 to 60 degrees. The outer surface of the distal end of the catheter is imprinted or otherwise marked with indicia indicating the location of underlying structural elements discussed in detail below. The overall dimensions of the catheter may be varied for patient anatomy, in the range of 45 to 70 cm long (for access to the coronary sinus from the subclavian vein percutaneous access point on the neck), 7 to 12 F in diameter at the distal end, and about 5 to 10 F internal diameter.

Figure 5:
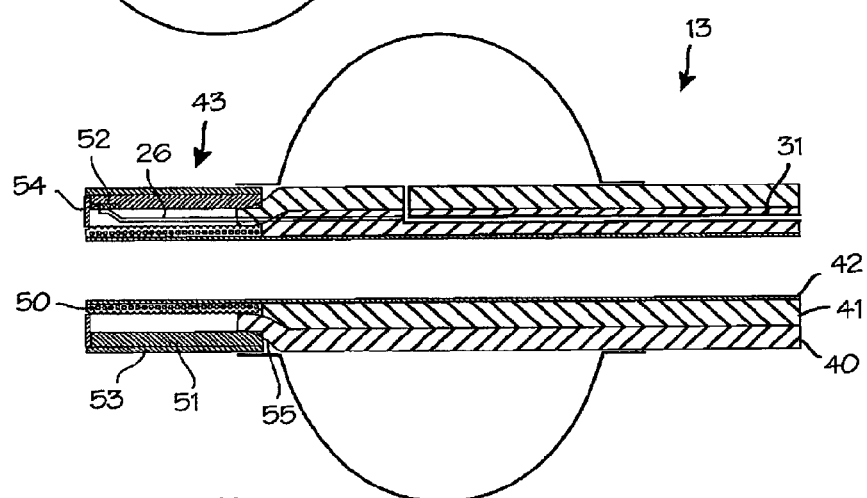
FIG. 5 shows a longitudinal cross-section of the guide catheter, in an embodiment which includes a deflection tube.
Figure 6:
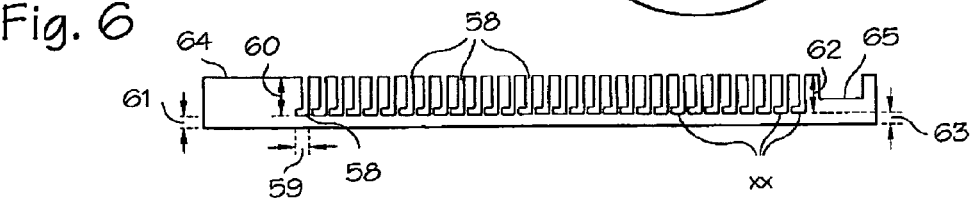
FIG. 6 shows a side view of the deflection tube from the guide catheter tubing assembly.

FIG. 5 shows and embodiment of the distal tip which includes a deflection tube assembly which helps control the direction of bending and the bend point of the distal tip. The distal assembly includes a covered coil 50, deflection tube 51, a pullwire anchor 52, deflection tube cover 53, and soft tip 54. The proximal end of the deflection tube is fitted over a necked down portion 55 of the catheter outer tube and glued in place. The deflection tube 51 is comprised of a round stainless steel, nitinol, or plastic tube with a specific pattern of slots machined into it (or formed during molding of a plastic tube) as shown in FIG. 6. The pattern of slots controls the shape that the distal portion of the catheter bends in and the sequence in which its sections bend. The preferred deflection tube is 0.110" OD, 0.100" ID, by 1.570" long. It has a pattern of thirty (30) slots 58 machined, ground, cut, lasered or EDM'ed into it. The slots 58 are spaced at a distance of 0.040" from one another. Each slot is 0.014" wide (referring to the longitudinal width, measured along the long axis of the tube). The slots maybe provided with hooked portions, and the length 59 of the hook portion may be about 0.032" long. The slots 58 are cut to varying depths in the deflection tube 51 to control the shape of the tube's bending. The most proximal slots are cut to a depth 60 of 0.090", leaving a spine thickness 61 of 0.010". The slots get progressively deeper from proximal to distal end, in groups of five (5). The final five (5) slots in the deflection tube 51 are cut to a depth 62 of 0.094", leaving a spine depth 63 of 0.006" in the deflection tube. The proximal unslotted portion of the deflection tube (marked as item 64 in FIG. 6) is joined to the necked down distal end of outer tube 40 as shown in FIG. 5.

Referring back to FIG. 5, the distal end of the pullwire is attached to the deflection tube 51 near the distal end of the device via an anchor 52. The anchor can be provided in the form of a C-shaped portion (a partial cylinder) that can be welded, soldered, brazed, glued or otherwise joined to the deflection tube, creating a unitary structure. The preferred design consists of a pullwire attached to a C-shaped portion of stainless steel tubing of the same diameter and thickness as the deflection tube 51. The C-shaped pullwire assembly is fit into a cavity 65 (FIG. 6) of the same size that has been machined out of the deflection tube 51. The pullwire can also be welded, glued, brazed or mechanically fixed to the inside of the deflection tube 51. The pullwire can alternately be affixed to a C-shaped section of nitinol or stainless steel tubing of the same or similar dimensions as the deflection tube itself.

Figure 7:
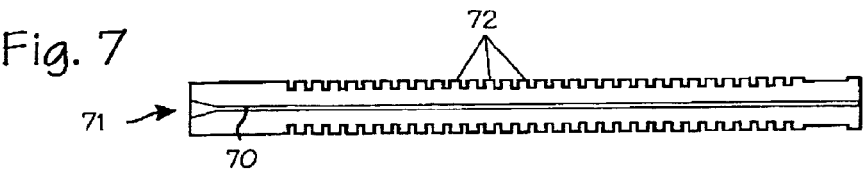
FIG. 7 shows a second view of the deflection tube from the guide catheter tubing assembly.

The deflection tube may be made of easily cut material such as plastic (suitable plastics include ABS, polycarbonate, acetal, nylon, polyethylene, polypropylene, PEBAX, polyurethane). If the strength and permanence of behavior of metal such as nitinol are desired, or easier cutting through a suitably stiff plastic, the deflection tube may be modified to permit easy slicing during removal, as shown in FIG. 7. The deflection tube may be provided with a deep score line, line of perforations or longitudinal slit 70, extending longitudinally through the tube, and further provided with the breech section 71 which will guide a cutting blade into the longitudinal slit. The breech section is an initial portion of the slot having an opening width wider than the slot which tapers into the slot. The score line, perforation line, or slot may be located along the spine of the deflection tube, as shown, or any be provided through the hoop portions 72 defined by the slots 58. Because the tube is closely trapped between layers of the catheter tube, the scoring or longitudinal slot does not significantly alter the impartation of a preferential bending axis to the catheter tip. The outer surface of the catheter can be marked with indicia indicating the location of the slot and breech section.

Figure 8:
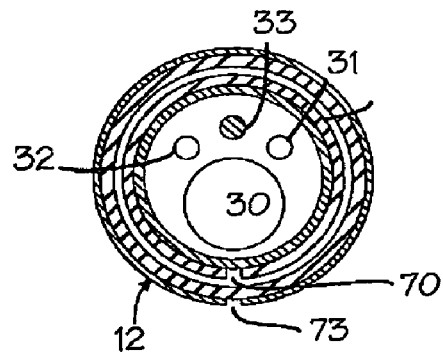
FIG. 8 is a radial cross section of the distal section of the catheter, in the area of the ring electrodes.

FIG. 8 shows a radial cross section of the distal tip of the catheter, in the vicinity of the ring electrodes. The catheter body tube includes the lumen 30 for passage of the pacemaker lead, a lumen 31 for balloon inflation, a lumen 32 for the sensing electrode wires, and a lumen for the steering pullwire 26, as shown in FIG. 3. The deflection tube 52 includes the longitudinal slit 70. The electrode may be very thin, so that it is easily cut with the cutter. If not, a gap 73 may be provided to permit easy cutting of the catheter in the area of the electrodes. The gaps in the deflection tube and the electrodes are preferably aligned with the thin wall of the catheter tube, and radially displaced from the pullwire and pullwire lumen as shown.

Figure 9:
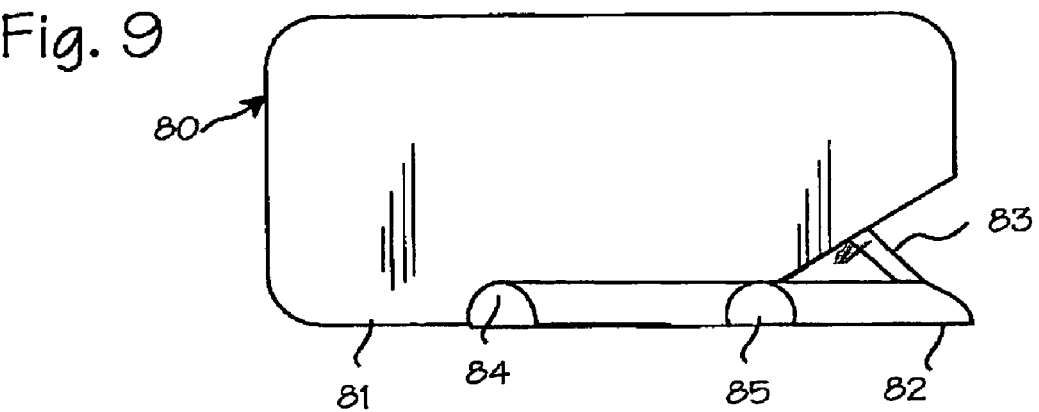
FIG. 9 illustrates a cutting tool suitable for use with the catheter.

FIG. 9 shows the cutter used with the catheter. The cutter 80 resembles a typical envelope opener, and comprises a handle 81, a protruding insertion guide 82, and a cutting blade 83 safely disposed at the base of the insertion guide between the insertion guide and the handle. The insertion guide is provided in a diameter or width that permits easy insertion into the lead lumen of the catheter, and in a length that provides, when inserted into the lumen, a mechanical guide for distal movement of the cutter along the axis of the catheter. The handle may be provided in any ergonomic form, for example, as shown, the handle is disposed substantially behind the cutting blade (taking the sharp edge of the blade as the front or distal orientation of the cutter). An arcuate guide or clamping tube 84, having an internal radius approximating the outer diameter of the pacemaker lead is disposed on the bottom of the handle, spanning from a point proximal to the blade, and from there extending proximally along the underside of the handle, may be provided to provide a secure grasp of the lead by the cutter, so that the lead is held in place, longitudinally, during proximal movement of the catheter body. An additional lead grasping element, in the form of an additional arcuate guide or clamping tube 85 may be provided on the distal end of the cutter, and can be used to hold the lead away from the catheter body during the removal of the catheter from the body.

In use, the surgeon implanting the pacemaker lead will first insert a hemostatic introducer sheath into the subclavian vein in the neck of patient, then insert a guide wire through the introducer sheath, and navigate the guide wire to the coronary sinus. Then, the surgeon slips the guide catheter onto the guide wire, and tracks it over the guide wire and into the subclavian vein through the introducer sheath. (The guide catheter EP leads are electrically connected to the EKG display through the EP connectors.) The guide catheter is navigated to the right atrium under fluoroscopic guidance or other visualization means. The surgeon must then steer and deflect the distal segment of the guide catheter, hunting for the ostium of the coronary sinus, to enter the coronary sinus. The surgeon confirms successful entry into the coronary sinus with the fluoroscopic images and EKG signals from the ring electrodes on the distal end of the guide catheter.

Once the tip of the guide is lodged in the coronary sinus, the surgeon inflates the balloon to block venous flow, and injects contrast agents as necessary to obtain a venogram and locate the desired coronary vein. After locating the coronary vein, the surgeon advances the guide wire into the desired coronary vein. The surgeon then passes the pacemaker lead over the guide wire, until the pacemaker lead tip is in the desired coronary vein, and seats the lead tip into the heart wall in the vein. (The lead tip need not leave the vein, and may be may be maneuvered until the surgeon confirms good electrical connection with the heart (good pacing and voltage thresholds are achieved) and then wedged in place within the vein.)

When placement is confirmed (electrically and fluoroscopically), the guide wire is pulled proximally and removed from the body, leaving the guide catheter with the pacemaker lead wire disposed within it in the body. To remove the guide catheter, the surgeon holds the slitter with the insertion guide in the lumen of the guide catheter, and holds the pacemaker lead wire with the cutter (either in the same hand, or with lead holders on the cutter), and pulls the guide catheter proximally, out of the body so that the wall of the guide catheter tube is pulled into the cutting blade of the cutter. When the distal section of the guide catheter is encountered, the surgeon can guide the cutter to cut along the indicia on the outside of the catheter or pass the blade through the gaps in the ring electrodes, to ensure that the cutter engages and cuts the weakened zones of the internal components.

Figure 10:
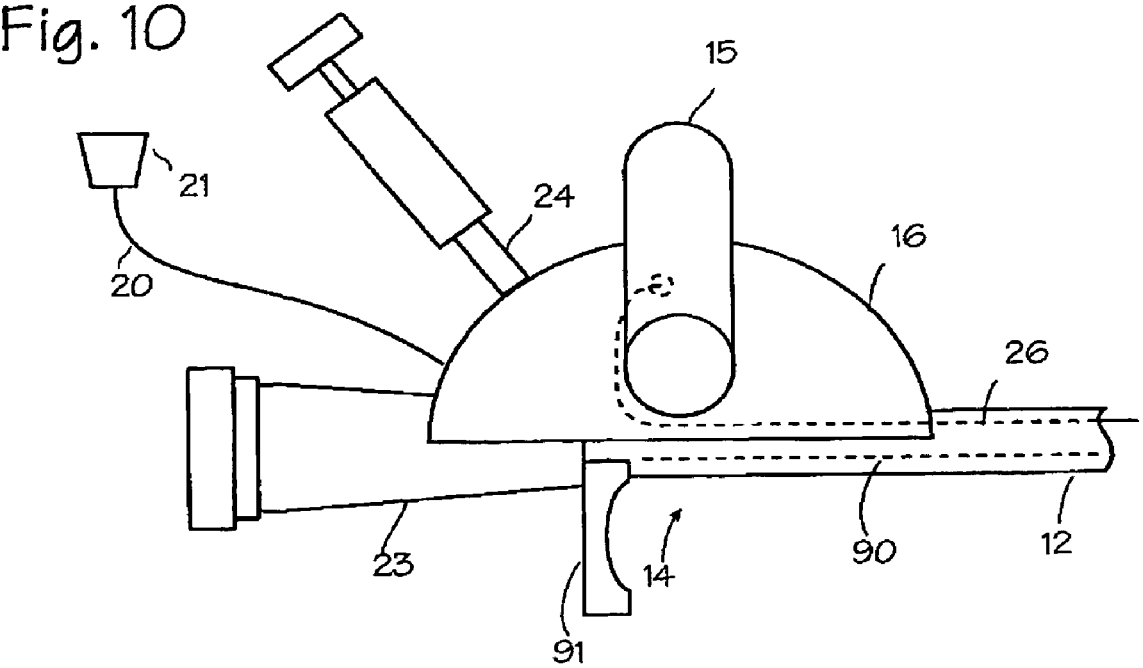
FIG. 10 illustrates a handle section of a steerable guide catheter which can be peeled apart during removal from the body.

FIG. 10 illustrates a handle section of a steerable guide catheter which can be peeled apart during removal from the body. The handle section includes many of the same elements and the handle section of FIG. 2, including the handle 16, the pullwire operator 15, the catheter body 12, the EP conductor 20 and EP connector 21, the hemostatic fitting 23. The pullwire 26 is shown attached to pullwire operator by affixing it to the proximal face of the cam 36, so that it runs under the pin 35. In this embodiment, the catheter body is scored or weakened along a score line 90, a matching score line on the other side of the catheter, to form a peelable strip within the catheter body. This peelable strip is an easily separable radial or circumferential segment of the catheter. The peeling tab 91 is fixed to the separable segment, and is useful as a handle to break the separable segment away from the handle and the remainder of the catheter and tear the separable segment from the other portion of the catheter. To accommodate the pacemaker connectors, the hemostatic fitting is provided with a lumen having an internal diameter large enough to allow the connectors to pass through the lumen.

In use, the surgeon may remove the guide catheter after lead placement by breaking a short proximal extent of the peelable portion of the catheter away from the handle, then pull the pacemaker connectors through the large lumen of the hemostatic fitting, and then withdraw the guide catheter from the body while pulling the peelable portion away from the catheter. The peelable portion may be supplanted by a zip strip embedded in the catheter body and attached to the peeling tab, and this sip strip may be used to split the catheter body open as it is pulled from the body. Alternatively, the pullwire may be used as the zip strip, and the surgeon may open the catheter by pulling the catheter proximally while pulling the handle, to which the pullwire is fixed, away from the pull tab and the remainder of the guide catheter.

The inventions describe above may be modified in various ways, and many of the features may be combined as desired. The materials suggested for the various components may be varied. The devices and methods may also be used to place leads or other elongate medical devices into the body, in any lumen of the body, though they have been explained and illustrated in the environment of pacemaker lead placement. Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A guide catheter system for placing a pacemaker lead into the heart of a patient, said pacemaker lead having a lead tip and a lead wire, the guide catheter system comprising:
   a guide catheter having a proximal end and a distal end, and an off-center lumen extending from the distal end to the proximal end;
   a deflection tube disposed within the distal tip of the catheter;
   a pullwire extending from the distal end to the proximal end, said pullwire operably coupled to the deflection tube;
   a handle fixed to the proximal end of the guide catheter, said handle comprising a grasping channel for grasping a circumferential portion of the guide catheter along a grasped length of the guide catheter, said circumferential portion being less than the full circumference of the guide catheter for the grasped length thereby defining an exposed portion of the guide catheter;
   a pull wire operator disposed on the handle and operably connected to the pullwire; and
   a cutter for cutting the guide catheter, said cutter having a blade sized and dimensioned to pass through the grasping channel of the handle while cutting the catheter body longitudinally.

2. The guide catheter system of claim 1 wherein:
   the deflection tube has a longitudinal slit extending therethrough, said slit being sized and dimensioned to permit passage of the cutter through the deflection tube.

3. The guide catheter system of claim 1 wherein:
   the deflection tube has a plurality of longitudinally disposed perforations extending therethrough, said perforations being sized and dimensioned to permit passage of the cutter through the deflection tube.

4. The guide catheter system of claim 1 wherein:
   the deflection tube has a longitudinally disposed scored line adapted to be cut by the cutter extending therethrough.

5. The guide catheter system of claim 1 further comprising:
   a balloon disposed on the distal tip of the guide catheter;
   a lumen communicating from the balloon to the proximal end of the catheter; and
   an inflation fitting providing fluid communication with the lumen at the proximal end of the guide catheter.

6. The guide catheter system of claim 1, further comprising at least one electrode disposed on the distal end of the catheter, wherein said electrode is adapted for sensing EKG signals emanating from body tissue.

7. The guide catheter system of claim 1, wherein the guide catheter further comprises:
   a braid embedded in the guide catheter, said braid comprised of plastic.

8. The guide catheter system of claim 1, wherein the guide catheter further comprises:
   a coil embedded in the distal end of the catheter, said coil comprised of plastic.

9. The guide catheter system of claim 1, wherein the guide catheter further comprises:
   a coil embedded in the distal end of the catheter, said coil comprised of metal wire having a diameter of not more than about 0.0025 inches.

* * * * *